United States Patent [19]

Korthoff

[11] Patent Number: 5,059,212

[45] Date of Patent: Oct. 22, 1991

[54] SURGICAL NEEDLE-SUTURE ATTACHMENT FOR CONTROLLED SEPARATION OF THE NEEDLE FROM THE SUTURE

[75] Inventor: Herbert W. Korthoff, Westport, Conn.

[73] Assignee: United States Surgical Corporation, Norwalk, Conn.

[21] Appl. No.: 532,913

[22] Filed: Jun. 4, 1990

Related U.S. Application Data

[63] Continuation-in-part of Ser. No. 413,240, Sep. 27, 1989.

[51] Int. Cl.$^5$ .............................................. A61B 17/00
[52] U.S. Cl. .................................... 606/224; 606/227
[58] Field of Search ................................ 606/224–228

[56] References Cited

U.S. PATENT DOCUMENTS

| | | |
|---|---|---|
| 86,769 | 2/1869 | Marriott . |
| 295,612 | 3/1984 | Bailey . |
| 299,305 | 5/1984 | Weed . |
| 877,476 | 1/1908 | Bach . |
| 1,106,667 | 8/1914 | Minahan . |
| 1,250,114 | 12/1917 | Bigelow et al. . |
| 1,558,037 | 10/1925 | Morton . |
| 1,591,021 | 7/1926 | Davis . |
| 1,613,206 | 1/1927 | Souttar .......................... 606/226 |
| 1,665,216 | 4/1928 | Morton et al. . |
| 1,678,361 | 7/1928 | Shearon . |
| 1,757,129 | 5/1930 | McClure . |
| 1,960,117 | 5/1934 | Lydeard . |
| 1,981,651 | 11/1934 | Logan . |
| 2,022,234 | 11/1935 | Everett . |
| 2,240,330 | 4/1941 | Flagg et al. ................... 606/226 |
| 2,302,986 | 11/1942 | Vollrath . |
| 2,411,079 | 11/1946 | Baule . |
| 2,802,468 | 8/1957 | Everett . |
| 2,814,296 | 11/1957 | Everett . |
| 2,910,983 | 11/1959 | Everett . |
| 2,928,395 | 3/1966 | Forbes et al. . |
| 3,311,110 | 3/1967 | Singerman et al. . |
| 3,394,704 | 7/1968 | Dery . |
| 3,416,534 | 12/1968 | Quinn . |
| 3,799,169 | 3/1974 | Beroff et al. . |
| 3,835,912 | 9/1974 | Kristensen et al. . |
| 3,875,946 | 4/1975 | Duncan . |
| 3,880,167 | 4/1975 | Hardwick . |
| 3,890,975 | 6/1975 | McGregor . |
| 3,910,282 | 10/1975 | Messer et al. . |
| 3,918,455 | 11/1975 | Coplan ............................. 606/225 |
| 3,924,630 | 12/1975 | Walldorg . |
| 3,926,194 | 12/1975 | Greenberg et al. . |
| 3,943,933 | 3/1976 | Gertzman . |
| 3,949,756 | 4/1976 | Ace . |
| 3,963,031 | 6/1976 | Hunter ............................. 606/227 |
| 3,980,177 | 9/1976 | McGregor ...................... 606/227 |
| 3,981,307 | 9/1976 | Borysko . |
| 4,054,144 | 10/1977 | Hoffman et al. . |
| 4,072,041 | 2/1978 | Hoffman et al. . |
| 4,124,027 | 11/1978 | Boss . |
| 4,127,133 | 11/1978 | Martinez . |
| 4,169,477 | 10/1979 | Bokros . |
| 4,359,053 | 11/1982 | Benjamin . |
| 4,411,654 | 10/1983 | Boarini et al. .................. 604/165 |
| 4,596,728 | 6/1986 | Yang et al. . |
| 4,624,879 | 11/1986 | Van Dijck et al. . |
| 4,672,734 | 6/1987 | Kawada et al. . |
| 4,792,336 | 12/1988 | Hlavaceh et al. ............... 623/13 |
| 4,805,292 | 2/1989 | Noguchi ............................. 29/445 |

FOREIGN PATENT DOCUMENTS

| | | |
|---|---|---|
| 0358451 | 5/1989 | European Pat. Off. . |
| 3223153 | 8/1983 | Fed. Rep. of Germany . |
| 2268534 | 11/1975 | France . |
| 2432861 | 3/1980 | France . |
| 512237 | 10/1971 | Switzerland . |

OTHER PUBLICATIONS

European Search Report for EP 90 31 05 21.
Raychem Corporation Product Specification RT–850 for Thermofit TM Kynar Tubing dated Mar. 6, 1984.

*Primary Examiner*—Stephen C. Pellegrino
*Assistant Examiner*—Gary Jackson
*Attorney, Agent, or Firm*—Thomas R. Bremer; Peter G. Dilworth; Rocco S. Barrese

[57] ABSTRACT

A combined surgical needle-suture device of controlled suture release characteristics and a method for manufacturing the device employ a shrinkable tubing to connect the needle to the suture. The tip of the suture which is connected to the needle possesses a reduced cross section relative to the remainder of the suture, such reduced cross section being capable of rupture by applying an amount of force therto, e.g., a sharp tug, within a predetermined range thus effecting needle separation.

24 Claims, 3 Drawing Sheets

SURGICAL NEEDLE-SUTURE ATTACHMENT FOR CONTROLLED SEPARATION OF THE NEEDLE FROM THE SUTURE

CROSS REFERENCE TO RELATED

This application is a continuation-in-part of commonly assigned, copending U.S. patent application Ser. No. 413,240, filed Sept. 27, 1989.

BACKGROUND OF THE INVENTION

The present invention relates to a method for attaching a surgical needle to a suture to provide a combined surgical needle-suture device possessing controlled suture release characteristics and, more particularly, to such a method in which a shrinkable tubing is employed to secure the needle to the suture.

For many years, surgeons have employed needle-suture combinations in which a suture or ligature is attached to the shank end of a needle. Such needle-suture combinations are provided for a wide variety of monofilament and braided suture materials, both absorbable and non-absorbable, e.g., catgut, silk, nylon, polyester, polypropylene, linen, cotton, and absorbable synthetic materials such as polymers and copolymers of glycolic and lactic acids.

Needle-suture combinations fall into two general classes: standard needle attachment and removable or detachable needle attachment. In the case of standard needle attachment, the suture is securely attached to the needle and is not intended to be separable therefrom, except by cutting or severing the suture. Removable needle attachment, by contrast, is such that the needle is separable from the suture in response to a force exerted by the surgeon. Minimum acceptable forces required to separate a needle from a suture (for various suture sizes) are set forth in the *United States Pharmacopoeia* (USP). The *United States Pharmacopoeia* prescribes minimum individual pull-out forces and minimum average pull-out forces as measured for five needle-suture combinations. The minimum pull-out forces for both standard and removable needle-suture attachment set forth in the *United States Pharmacopoeia* are hereby incorporated by reference.

One typical method for securing a suture to a needle involves providing a cylindrical recess in the shank end of a needle and securing a suture therein. For example, U.S. Pat. No. 1,558,037 teaches the addition of a cement material to such a substantially cylindrical recess to secure the suture therein. Additional methods for bonding a suture within a needle bore are described in U.S. Pat. Nos. 2,928,395 (adhesives) and 3,394,704 (bonding agents). Alternatively, a suture may be secured within an axial bore in a needle by swaging the needle in the region of the recess. See, e.g., U.S. Pat. No. 1,250,114. Additional prior art methods for securing a suture within a needle bore include expansion of a catgut suture through the application of heat (U.S. Pat. No. 1,665,216), inclusion of protruding teeth within the axial bore to grasp an inserted suture (U.S. Pat. No. 1,678,361) and knotting the end of the suture to be inserted within the bore to secure the suture therein (U.S. Pat. No. 1,757,129).

Methods for detachably securing a suture to a needle are also well known. For example, U.S. Pat. Nos. 3,890,975 and 3,980,177 teach swaging a suture within a needle bore such that the suture has a pull-out valve of 3 to 26 ounces. Alternative detachable attachment methods include providing a weakened suture segment (U.S. Pat. No. 3,949,756), lubricant tipping the end of a suture to be inserted in the axial bore of a needle (U.S. Pat. No. 3,963,031) and pre-tensioning a suture that is swaged within an axial needle bore (U.S. Pat. No. 3,875,946). See also, U.S. Pat. Nos. 3,799,169; 3,880,167; 3,924,630; 3,926,194; 3,943,933; 3,981,307; 4,124,027; and, 4,127,133.

Another method for attaching a suture to a needle involves the use of tubing which is secured to the shank end of the needle and to the suture. For example, U.S. Pat. No. 1,613,206 describes the use of a tubing (preferably silver) which is secured to the shank end of a needle and to a ligature. It is suggested that the tube may be attached to the needle by pressure or soldering and to the ligature by pressure or cementing. It is also suggested that the shank of the needle be of reduced cross section and that the furthest extremity of the reduced diameter shank section be provided with a spike or point upon which the suture may be secured prior to tube application.

U.S. Pat. No. 2,240,330 describes a tubing attachment method whereby the tubing and suture are releasably secured to the needle. In particular, the needle and tubing are provided with cooperating catch and abutment means which are released one from the other by rotating the needle 90° relative to the tubing (or vice versa). The tubing is manufactured from spring-tempered carbon steel or chrome nickel steel and is secured to the suture by heating the tubing and then swaging to the suture.

U.S Pat. No. 3,311,100 relates to a flexible composite suture having a tandem linkage. The needle is secured to a flexible suture leader manufactured from a readily sterilizable plastic such as nylon, linear polyethylene, isotactic polypropylene, polyester, silk or other proteinaceous material, e.g., by inserting and crimping the leader within an axial bore in the needle shank. The opposite end of the suture leader is crimped within a connector sleeve of a thin walled metal tubing, e.g., stainless steel. The opposite end of the tubing is crimped around a stiff suture, e.g., monofilament stainless steel.

U.S. Pat. No. 3,918,455 describes a needle-suture attachment wherein a hollow suture portion is secured to the shank end of a needle which is of reduced cross-section as compared to the remainder of the needle.

Additional patents which describe the use of tubing to effect suture-needle attachment include U.S. Pat. Nos. 4,672,734 (forming needle from U-shaped metal plate around suture), 4,359,053 (silicone tubing), 3,835,912 (laser welding of metal tube to needle), 2,814,296, 2,802,468 (chamfered tubing ends), 2,302,986, 2,240,330, 1,981,651 (needle and tubing screw threaded), 1,960,117, and 1,591,021.

Numerous disadvantages exist with methods used heretofore to effect needle-suture attachment. For example, those methods which involve the formation and use of an axial bore in the shank end of the needle require the use of expensive hole forming equipment. Moreover, it is difficult to maintain the bore concentric with the center-line of the needle and to control the depth (and diameter) of the bore when drilling the needle shank, whether using conventional drilling equipment or laser drilling. Another disadvantage is the possibility that foreign substances may inadvertently or uncontrollably be introduced into the needle bore, e.g., oil used during drilling or silicone from the needle silconization process. Safeguards employed in an attempt to prevent the introduction of such foreign materials, e.g., water blocking during needle silconization, are inconvenient adding time, effort and cost to the needle production process.

Attachment processes which employ bored needle shanks also limit the range of materials from which needles may be fabricated in a cost effective fashion. For example, it is exceedingly difficult to drill Series 300 stainless steel (laser drilling is required) and, once drilled, it is difficult to swage Series 300 stainless steel in a consistent and reliable manner. For this reason, Series 300 stainless steel is not employed for the vast majority of needled suture products despite its advantageous combination of strength and ductility characteristics as compared to conventionally employed Series 400 stainless steel.

Additional disadvantages associated with needle-suture attachment methods which employ bored needle shanks include the weakness imparted to the bored section of the needle, particularly after swaging, and the attendant increased possibility that the needle will fracture in this region. It is also difficult to provide a specialized surface finish to the needle shank to assist in needle attachment, e.g., a texturized surface and/or a tapered bore. Swaging equipment used in such needle-suture attachment methods is also maintenance intensive.

Needle-suture attachment methods which have employed tubings heretofore also exhibit numerous disadvantages. Methods which employ metal tubings greatly diminish the flexibility of the needle-suture combination in the attachment region. Such diminished flexibility has a deleterious effect in many surgical procedures. Swaging of the tubing to the needle and the suture is also undesirable in that swaging is time-consuming, maintenance intensive, and subject to variability in attachment force.

Moreover, needle-suture attachment methods which have employed tubings heretofore have necessarily required the use of tubing having an inner diameter essentially equal to the outer diameters of the needle shank and suture tip to be attached. Too large a difference between the aforesaid inner and outer diameters inhibits the attachment process, and prevents a tight, secure interface between needle (and/or suture) and tubing. The limited tolerance between the tubing inner diameter and the needle shank/suture outer diameters in such methods make these dimensions critical, thereby making the attachment process more difficult and time-consuming, and increasing the likelihood of attachment failure and/or rejected materials.

Commonly assigned, copending U.S. patent application Ser. No. 413,240, filed Sept. 27, 1989, of which the present application is a continuation-in-part, describes and claims a combined surgical needle-suture device and surgical needle-suture attachment method which overcomes the aforementioned drawbacks of the previously known needle-suture combinations and needle-suture attachment methods. In accordance with said application, a combined surgical needle-suture device is provided in which a surgical needle having a shank of reduced cross-section is attached to a suture through a shrinkable tubing, or microferrule, which is fitted about the needle shank and a portion of the suture. Application of energy to the shrinkable tubing brings the tubing into engagement with both the needle shank and the suture. The physical and chemical characteristics of the shrinkable tubing material, the relative diameters of the tubing, the needle shank and the suture, and the amount of energy applied to the tubing may be controlled to provide a needle-suture combination having a desired pull-out force. It is thus possible to produce standard needle-suture combinations and removable needle-suture combinations using a single attachment process and a common inventory of materials.

Minimum average pull-out forces for various sizes combined surgical needle-suture devices are set forth in the *United States Pharmacopoeia* and are as follows:

| Suture Size | Average Pull-Out Force/Ounces |
| --- | --- |
| 8/0 | 2.39 |
| 7/0 | 3.20 |
| 6/0 | 5.92 |
| 5/0 | 7.97 |
| 4/0 | 15.97 |
| 3/0 | 23.63 |
| 2/0 | 38.80 |
| 1/0 | 52.89 |
| 1 | 63.48 |
| 2 and larger | 63.48 |

U.S. Pat. No. 3,875,946, referred to supra, describes needle-suture combinations said to exhibit suture pull-out values that are substantially less than those given by the *United States Pharmacopoeia* as set forth above. According to U.S. Pat. No. 3,875,946, employing the procedure described therein, combined surgical needle-suture devices can be obtained with the following average pull out forces:

| Suture Size | Average Pull-Out Force/Ounces |
| --- | --- |
| 8/0 | 1–2 |
| 7/0 | 1–3 |
| 6/0 | 2–5 |
| 5/0 | 3–7 |
| 4/0 | 3–15 |
| 3/0 | 3–23 |
| 2/0 | 3–26 |
| 1/0 | 10–26 |
| 1 | 10–26 |
| 2 and larger | 10–26 |

These pull-out forces are obtained by prestressing the suture, i.e., by applying tension to the suture after the tip of the suture has been inserted into an axial bore, or recess, formed in the blunt end of the needle and the needled suture has been swaged so that the force required to pull the suture out of the recess exceeds the minimum limits on needle attachment set forth in the *United States Pharmacopoeia* but is less than the actual tensile strength of the suture used. As the suture is pulled from the needle during application of the tensioning force, the force required to move the suture relative to the swaged section decreases. When the tensioning force required to move the end of the suture relative to the needle recess drops to the desired pull-out value, the tension is released.

The foregoing procedure is said to permit better control of the resulting needle-suture device in that the force required to separate a suture of a particular size from its attached needle is uniform.

In the approach to achieving controlled needle-suture separation described in aforementioned U.S. Pat. No. 3,926,194, the contents of which are incorporated by reference herein, a suture having a reduced diameter or cross section at its tip is inserted into the recess formed in the blunt end of the needle. This reduced suture material region results in a rupture strength which is lower than the rupture strength in other portions of the suture and lower than the force necessary to pull the suture tip out of the needle recess. The rupture strength can be controlled to a value which results in the separation of the needle from the suture by a sharp tug which can fall within the range of average pull-out forces set forth above, i.e., 1 to 26 ounces depending on suture size.

SUMMARY OF THE INVENTION

In accordance with the present invention, there is provided a method for attaching a surgical needle to a suture to provide a combined surgical needle-suture device exhibiting a predetermined range of average rupture force to effect separation of the needle from the suture which comprises:

a) providing a surgical needle having a shank end of reduced cross-section and a suture having a region of reduced cross section at its tip;

b) placing a shrinkable tubing around the reduced diameter shank of the needle and the tip of the suture having the region of reduced cross section with a portion of the reduced cross section region extending beyond the shrinkable tubing; and, c) applying energy to the shrinkable tubing to bring the tubing into engagement with the needle shank and suture thereby providing a combined surgical needle-suture device in which the force required to achieve rupture of the suture at its region of reduced cross section with consequent separation of the needle from the suture falls within a predetermined average value.

In addition to the foregoing surgical needle-suture attachment method, the present invention includes the resulting combined surgical needle-suture device.

BRIEF DESCRIPTION OF THE DRAWINGS

The present invention will become more apparent from the following detailed description taken in conjunction with the accompanying drawings in which.

DETAILED DESCRIPTION OF THE INVENTION

The present invention relates to a combined surgical needle-suture method and resulting surgical needle-suture device featuring controlled suture release. The invention has application to any suture material whether absorbable or non-absorbable, natural or synthetic, braided or monofilament, and to any needle material and configuration whether straight or curved.

Figure 1:
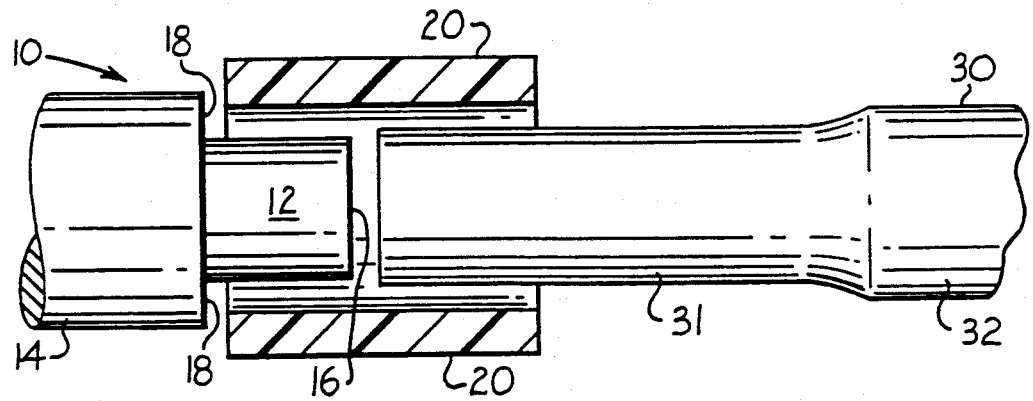
FIG. 1 is a side cross-sectional view of a surgical needle possessing a shank of reduced diameter and a suture possessing a region of reduced diameter at its tip with a shrinkable tubing positioned around the needle shank and the suture tip (prior to engagement of the tubing with the needle and suture)
Figure 2:
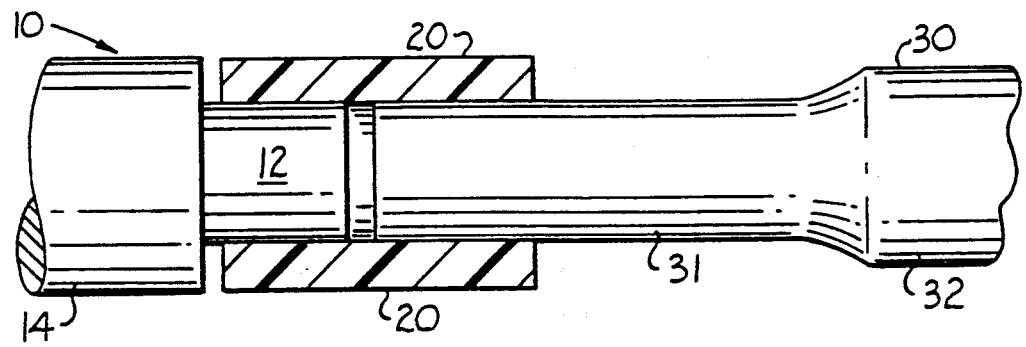
FIG. 2 is a side cross-sectional view of the needle and suture combination of FIG. 1 following shrinking of the tubing to effect engagement of the needle and suture.
Figure 3:
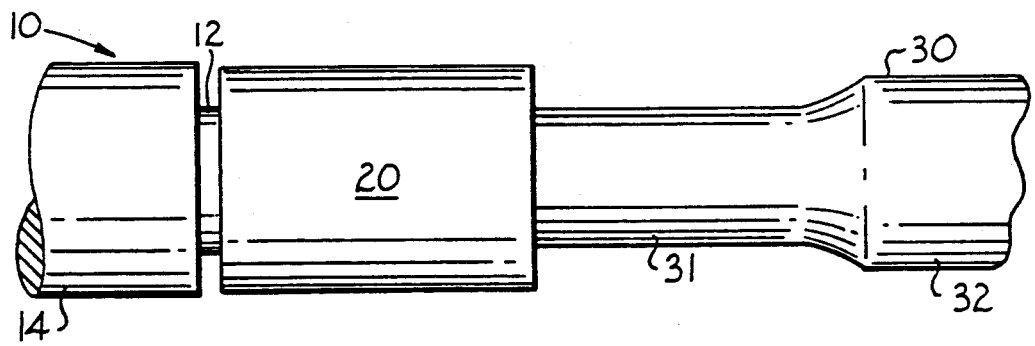
FIG. 3 is a side view of the combined surgical needle-suture device of FIG. 2.
Figure 4:
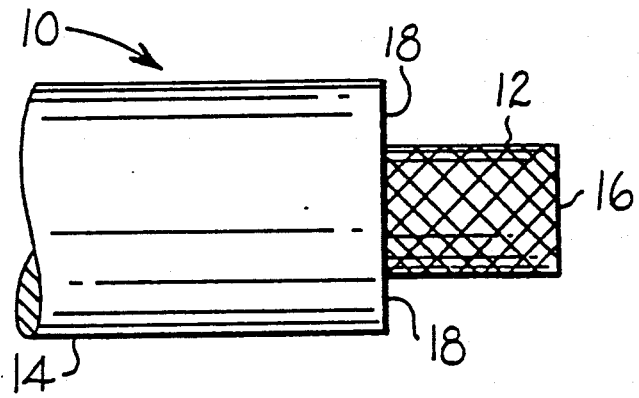
FIG. 4 is a side view of an alternative embodiment of the present invention in which the shank of the needle is scored.
Figure 5:
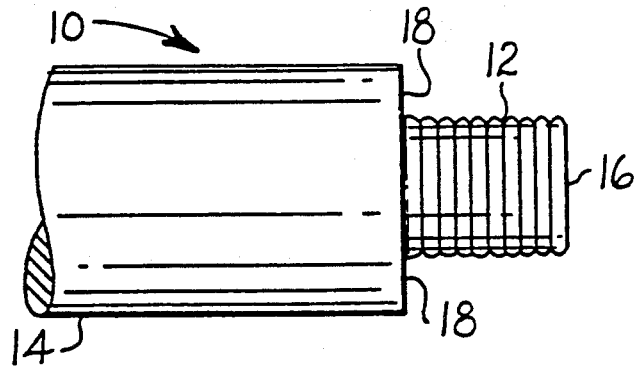
FIG. 5 is a side view of an alternative embodiment of the present invention in which the needle shank is ribbed.
Figure 6:
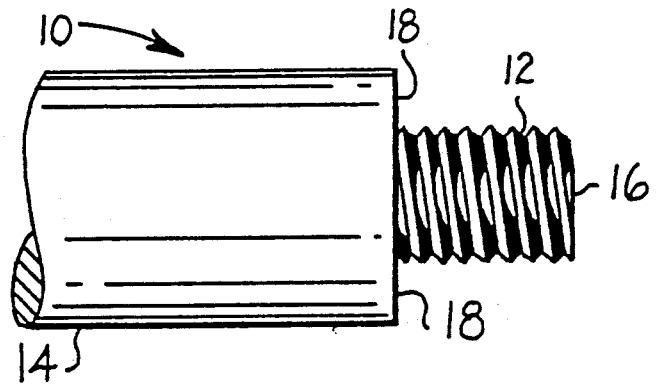
FIG. 6 is a side view of an alternative embodiment of the present invention in which the needle shank is threaded.
Figure 7:
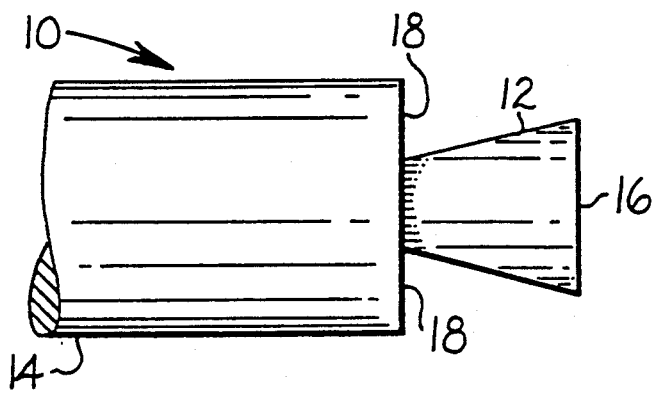
FIG. 7 is a side view of an alternative embodiment of the present invention in which the needle shank is flared in a direction away from a remainder of the needle.
Figure 8:
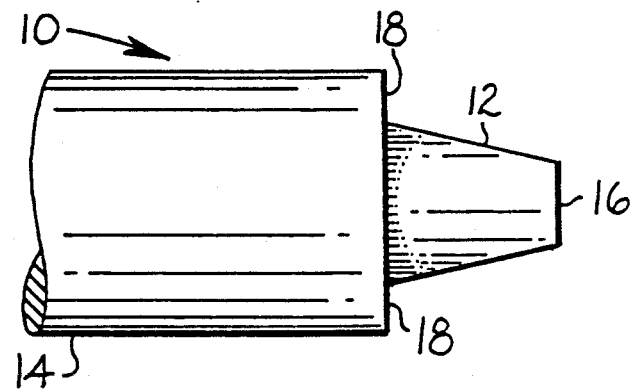
FIG. 8 is a side view of an alternative embodiment of the present invention in which the needle shank is tapered in a direction towards the remainder of the needle.

Referring to FIGS. 1-3, needle 10 has a reduced cross-sectional diameter at its shank end 12 relative to the remainder of needle 14. The diameter of shank end 12 can be reduced by any conventional means, e.g., by machining on a lathe. Typically, shank end 12 has a diameter from 10 to 65% smaller than the remaining portion 14 of the needle, and preferably from 25 to 50% smaller. It is also possible to provide shank end 12 with a texturized surface to facilitate gripping by shrinkable tubing 20. For example, shank end 12 can be scored, ribbed or threaded, in whole or in part (FIGS. 4-6 respectively). It may also be desirable to taper shank end 12 such that its butt, or distal, end 16 is of greater cross-sectional diameter than the cross-sectional diameter of shank end 12 in the region of shoulder 18, or vice versa (FIGS. 7 and 8 respectively). Shank end 12 is placed within tubing 20 as shown in FIG. 1.

The sutures suitable for use in the preparation of the notched needle-suture combination herein include both monofilaments and multifilament structures such as braided, twisted and covered sutures. Suitable suture materials include collagen (including catgut and extruded collagen), silk, cotton, linen and synthetic polymers including nylon, polypropylene and polyesters such as polyethylene terephthalate and homopolymers and copolymers of lactide and glycolide.

With multifilament sutures, the entire cross-sectional area of the suture is not made up of suture material since there is, of necessity, some free space between the suture strands. The proportion of the total cross-sectional area of a suture which is occupied by the suture strands is called "suture density". As disclosed is aforementioned U.S. Pat. No. 3,926,194, the suture densities of braided structures and suture densities in general are calculated from the volume of the sample of the suture and the volume of the fiber therein in accordance with the formula:

$$D = \frac{F}{S}$$

in which S is the volume of the suture, F is the volume of the fiber, and D is the suture density.

For convenience, it is best to determine volumes in samples at fixed lengths of 9,000 meters, r $9 \times 10^5$ centimeters. This is convenient because fiber denier is defined as weight in grams per 9,000 meters. At this length, the volume of the suture in cubic centimeters is:

$$\frac{\pi d^2 (9 \times 10^5)}{4}$$

where d is the diameter of the suture in centimeters. The volume in cubic centimeters of the individual fibers, F, at the same length would be:

$$\frac{\text{number of strands} \times \text{denier per strand}}{r}$$

or $$\frac{\text{denier of suture}}{r}$$

where r is the density of the suture material in grams per cubic centimeter.

As further disclosed in U.S. Pat. No. 3,926,194, the load at which reduced tip suture 30 will rupture within its region of reduced diameter can be estimated from the equation:

$$P = \frac{ATD}{K}$$

wherein

P is the rupture load, in pounds;

T is the tensile strength of the suture material, in pounds per square inch;

A is the area, in square inches, of the reduced diameter portion of the suture;

D is the suture density of the suture, being unity in the case of a monofilament; and, K is a constant factor, empirically determined and representing the degree of weakening at the reduced tip portion of the suture over and above the weakening to be expected from its reduced area.

The extent of the diameter, or cross-sectional area, reduction of tip region 31 will be such as to result, following attachment of the needle and suture as described below, in an average rupture force within a predetermined range. For example, a suitable range of rupture force in ounces and in pounds for various suture sizes can be as follows:

| Suture Size | Average Rupture Force | |
|---|---|---|
| | Ounces | Pounds |
| 8/0 | 1–2 | .0625–.125 |
| 7/0 | 1–3 | .0625–.1875 |
| 6/0 | 2–5 | .125–.3125 |
| 5/0 | 3–7 | .1875–.4375 |
| 4/0 | 3–15 | .1875–.9375 |
| 3/0 | 3–23 | .1875–1.4375 |
| 2/0 | 3–26 | .625–1.625 |
| 1/0 | 10–26 | .625–1.625 |
| 1 | 10–26 | .625–1.625 |
| 2 and larger | 10–26 | .625–1.625 |

Selecting, e.g., an average rupture value P of 0.8 pounds provides leeway for differences in individual sutures and for differences in the reduction of their tips and assures rupture strengths within the desired range for most of the reduced tip sutures. The value of constant factor K can be experimentally determined for each suture material by comparing the actual breaking strength of a reduced diameter suture to the strength calculated on the basis of the tensile strength of the material and the diameter of the reduced tip. For example, a sample of chromic catgut is known to have a tensile strength of from 45,000–65,000 psi with an average tensile strength of 55,000 psi. A size 5/0 catgut would accordingly be expected to have a breaking strength of 1.85 pounds. When the tip of a 2/0 catgut is reduced to size 5/0, however, the breaking strength is determined to be 1.4 pounds, and a value for K is computed as 1.85/1.4 or 1.3. Values of K for other suture materials are readily determined in a like manner.

In general, tip 31 will be reduced in cross section by at least about 10% relative to remaining region 32 of suture 30. Reduction of the material in the tip region of suture 30 to provide the region of reduced cross-section at tip 31 can be accomplished in a variety of ways, e.g., as described in U.S. Pat. No. 3,926,194. Thus, the suture tip can be ground down to the desired diameter and to the desired length of the cutaway portion. The grinding can be carried out by known techniques and in known equipment such as in a jeweler's lathe or in a grinding machine as described in British Patent No. 1,180,276. Another tip reduction method which is applicable to monofilament sutures is to produce a continuous monofilament with spaced segments of reduced diameter, each such segment being cut to provide two reduced diameter suture ends. A continuous filament of this type can be prepared by providing pulsation during the extrusion of the monofilament, or periodic partial slowdown of the rate of polymer feed to the extrusion orifices.

The procedure for attaching needle 10 to suture 30 employing shrinkable tubing 20 will now be described.

Suture 30 is positioned within shrinkable tubing 20 with suture tip 31 abutting or separated a short distance from distal end 16 of shank 12. Prior to insertion into tubing 20, tip region 31 of suture 30 can, if desired, be tipped with an adhesive or resinous agent as disclosed, e.g., in Canadian Patent No. 1,009,532, to prevent brooming, particularly for multifilament braided sutures, and/or to facilitate attachment of the needle using the shrinkable tubing of the present invention.

After shrinkable tubing 20 is placed around shank end 12 of needle 10 and suture tip region 31, energy is applied to tubing 20. In response to this energy, tubing 20 contracts or shrinks and engages shank end 12 and suture 30. The overall length of tubing 20 may also be affected by the application of energy, e.g., the length of tubing 20 may reduce. Thus, the shrinking of tubing 20 brings the inner surface of tubing 20 into engagement with shank end 12 and suture 30 thereby securing suture 30 to needle 10. Suitable energy sources include heat (convective or conductive), radiation, microwave energy, etc.

As shown in FIGS. 1–2, shrinkable tubing 20 is simultaneously placed around both suture 30 and shank end 12 of needle 10 in one embodiment of the present invention. It is preferable, however, to sequentially secure tubing 20 to the shank end 12 of needle 10 and thereafter to tip 31 of suture 30. Thus, in a preferred embodiment of the present invention, shrinkable tubing 20 is initially secured to shank end 12 through the localized application of energy to tubing 20 in the region surrounding shank end 12. After tubing 20 has been brought into engagement with shank end 12, tip region 31 of suture 30 is inserted into tubing 20 and additional energy is applied thereto. Sequential shrinkage of tubing 20 makes it possible to vary the amount of energy used in securing tubing 20 to shank end 12 and suture tip 31, respectively, and to limit the exposure of suture 30 to energy during the attachment process. It may also be desirable to cool suture 30 in the region outside tubing 20 to prevent any undesirable degradation thereof, e.g., employing a cold air curtain.

As shown in FIGS. 2-3, the shrinkage of tubing 20 typically compresses suture 30 to some extent. This is particularly true where the suture is a braided, multifilament material having void spaces in its structure. For example, tubing 20 may compress suture 30 by as much as 30 to 35% for a braided, synthetic absorbable suture and by a minimal amount for a relatively stiff material such as a monofilament surgical gut.

Shrinkable tubing 20 can be manufactured from any material which shrinks, i.e., reduces in diameter, in response to the application of energy. Suitable materials include "memory metals," e.g., nickel-titanium mixtures, nickel-iron-titanium mixtures, or copper based materials, as are well known in the art (see, e.g., U.S. Pat. Nos. 3,759,552, 3,801,954, 4,198,081, and 4,773,680), and shrinkable plastic materials, such as polyvinylidene fluoride materials available from Raychem Corporation, Menlo Park, California, under the tradename Kynar. In the case of shrinkable plastic materials, the tubing is typically extruded such that the inner diameter is less than the final desired inner diameter, i.e., the inner diameter of the tubing after energy application in the attachment method of the present invention. Thereafter, the extruded tubing is expanded radially outward through radial expansion means to provide a tubing of expanded inner diameter as shown, for example, by tubing 20 in FIG. 1. Such plastic tubing is thus adapted to shrink, or "recover", to its original extruded inner diameter in response to the application of a predetermined amount of energy.

The amount of energy applied to the tubing to effect the desired attachment, i.e., diameter reduction, depends upon the chemical characteristics of the tubing material and the relative dimensions of the tubing, the shank end of the needle and the suture. For example, one polyvinylidene fluoride material available from Raychem Corporation (RT-850) shrinks at temperatures greater than 175° C. and is adapted to recover to about 50% of its radially expanded inner diameter. In such case, tubing 20 can be brought into engagement with shank end 12 of needle 10 and tip 31 of suture 30, either simultaneously or sequentially, by heating tubing 20 to a temperature above 175° C. Tubing 20 can be heated through contact with a hot gas stream or with heated dies, or by other heating means. Typically, the outer diameters of shank end 12 and suture tip region 31 (in the region inserted into tubing 20) are greater than the fully recovered diameter of tubing 20, e.g., greater than 50% of the initial inner diameter of tubing 20 for the RT-850 material such that tubing 20 engages shank end 12 and suture tip 31. It is preferred that the attachment conditions be controlled such that the tubing remains secured to the needle once the suture is detached.

The foregoing surgical needle-suture attachment procedure has many advantages over previous attachment methods. Machining of the needle to provide a reduced diameter needle shank is much easier and more controllable than drilling processes, and permits the use of needle alloys which have previously been impractical, e.g., Series 300 stainless steel and MP35N (available from SPS Technologies). These heretofore impractical alloys have advantageous strength and ductility characteristics as compared to conventionally used Series 400 stainless steels. Moreover, an unreliable, expensive and maintenance intensive swaging process is replaced by a sterile, controllable and relatively inexpensive energy supply. The tubing used in the present invention may be color coded to designate suture material, standard versus detachable attachment, etc., particularly where a plastic tubing is employed.

The attachment method is also much more efficient from a processing and inventory control standpoint. For example, the tubing can be removed from a needle and the needle attached to a fresh suture as may be the case where the suture and/or attachment properties of the initial suture-needle combination are outside specifications. In many instances, the suture can also be recovered and reused thereby greatly reducing processing waste. The range of acceptable suture diameters is greatly expanded due to the ability of the tubing to recover or shrink to varying degrees thereby minimizing the likelihood that suture production will be rejected for inability to attach several needle sizes because the shrinkable tubing is capable of recovering or shrinking to varying degrees. This greatly simplifies inventory considerations. Moreover, the needle-suture combinations are atraumatic and advantageously exhibit flexibility in the attachment region.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A method for attaching a surgical needle to a suture to provide a combined surgical needle-suture device exhibiting a predetermined range of average pull-out force for a suture of given size which comprises:
   a) providing a surgical needle having a shank end of reduced cross-section and a suture having a region of reduced cross section at its tip;
   b) placing a shrinkable tubing around the reduced diameter shank of the needle and the tip of the suture having the region of reduced cross section with a portion of the reduced cross section region extending beyond the shrinkable tubing; and,
   c) applying energy to the shrinkable tubing to bring the tubing into engagement with the needle shank and suture thereby providing a combined surgical needle-suture device in which the force required to achieve rupture of the suture at its region of reduced cross section with consequent separation of the needle from the suture falls within a predetermined average value.

2. The method of claim 1 wherein the predetermined average value of the rupture for a particular size of suture is as follows:

| Suture Size | Average Rupture Force/Ounces |
| --- | --- |
| 8/0 | 1-2 |
| 7/0 | 1-3 |
| 6/0 | 2-5 |
| 5/0 | 3-7 |
| 4/0 | 3-15 |
| 3/0 | 3-23 |
| 2/0 | 3-26 |
| 1/0 | 10-26 |
| 1 | 10-26 |
| 2 and larger | 10-26 |

3. The method of claim 1 wherein the cross section of the tip of the suture is reduced by at least 10% relative to the cross section of the remaining suture.

4. The method of claim 1 wherein the suture is a monofilament suture.

5. The method of claim 1 wherein the suture is a multifilament suture.

6. The method of claim 1 wherein the step of applying energy further comprises applying energy to bring the tubing into engagement with the needle shank and thereafter applying energy to shrink the shrinkable tubing into engagement with the tip of the suture.

7. A combined surgical needle-suture device which comprises:
   (a) a needle having a shank of reduced cross-section;
   (b) a suture having a region of reduced cross section at its tip; and,
   (c) a shrinkable tubing around said needle shank and a portion of the region of reduced cross section of the tip of the suture to couple the same without swaging or crimping, the force required to achieve rupture of the suture at its region of reduced cross section and consequently, separation of the needle from the suture, falling within a predetermined average value.

8. The combined surgical needle-suture device of claim 7 wherein the predetermined average value of the rupture force for a particular size of suture is as follows:

| Suture Size | Average Rupture Force/Ounces |
|---|---|
| 8/0 | 1-2 |
| 7/0 | 1-3 |
| 6/0 | 2-5 |
| 5/0 | 3-7 |
| 4/0 | 3-15 |
| 3/0 | 3-23 |
| 2/0 | 3-26 |
| 1/0 | 10-26 |
| 1 | 10-26 |
| 2 and larger | 10-26 |

9. The combined surgical needle-suture device of claim 7 wherein the cross section of the tip of the suture is reduced by at least 10% relative to the cross section of the remaining suture.

10. The combined surgical needle-suture device of claim 7 wherein the suture is a monofilament suture.

11. The combined surgical needle-suture device of claim 7 wherein the suture is a multifilament suture.

12. The combined surgical needle-suture device of claim 7 wherein said suture is a non-absorbable material selected from the group consisting of silk, nylon, polyester, polypropylene, linen and cotton.

13. The combined surgical needle-suture device of claim 7 wherein said suture is a braided multifilament.

14. The combined surgical needle-suture device of claim 7 wherein said suture is a monofilament.

15. The combined surgical needle-suture device of claim 7 wherein said suture is an absorbable material selected from the group consisting of gut and synthetic materials including polymers and copolymers of glycolic and lactic acids.

16. The combined surgical needle-suture device of claim 15 wherein said suture is a braided multifilament.

17. The combined surgical needle-suture device of claim 7 wherein said suture portion is tipped with an adhesive or resinous coating.

18. The combined surgical needle-suture device of claim 7 wherein said shrinkable tubing is manufactured from a memory metal or a shrinkable plastic material.

19. The combined surgical needle-suture device of claim 18 wherein said shrinkable plastic material is a polyvinylidene fluoride material.

20. The combined surgical needle-suture device of claim 7, wherein the shank is provided with a texturized surface to facilitate gripping by said shrinkable tubing.

21. The combined surgical needle-suture device of claim 20, wherein the shank is scored, ribbed, or threaded in whole or in part.

22. The combined surgical needle-suture device of claim 7, wherein the shank of reduced cross section forms a shoulder with a remainder of said needle.

23. The combined surgical needle-suture device of claim 22, wherein said shank is tapered in a direction towards said shoulder, such that a distal end of said shank is of greater cross-sectional diameter than cross-sectional diameter of said shank in a region of said shoulder.

24. The combined surgical needle-suture device of claim 23, wherein said shank is tapered in a direction away from said shoulder, such that a distal end of said shank is of smaller cross-sectional diameter than cross-sectional diameter of said shank in a region of said shoulder.

* * * * *